United States Patent [19]

Hsu

[11] Patent Number: 4,684,609

[45] Date of Patent: Aug. 4, 1987

[54] METHOD AND SUBSTANCE FOR THE ENHANCED LABELLING OF CELLULAR MATERIAL

[75] Inventor: Su-Ming Hsu, Seekonk, Mass.

[73] Assignee: Vector Laboratories, Inc., Burlingame, Calif.

[21] Appl. No.: 273,813

[22] Filed: Jun. 15, 1981

[51] Int. Cl.$^4$ .................... G01N 33/54; C12N 9/96
[52] U.S. Cl. .................... 435/7; 435/188; 435/810; 436/519; 436/547
[58] Field of Search .................... 435/7, 28, 188, 810; 424/8, 12, 1, 1.5; 23/230 B; 436/547, 519

[56] References Cited

U.S. PATENT DOCUMENTS 4,228,237 10/1980 Hevey et al. .................... 424/12
4,298,685 11/1981 Parikh et al. .................... 435/810

OTHER PUBLICATIONS

Hsu et al, "A Comparative Study of the Peroxidase-Anti-Peroxidase Method and an Avidin-Biotin Complex Method for Studying Peptide . . . ", American Journal of Clinical Pathology, 75(5) (1981), pp. 734–738, Chemical Abstracts 95:20759u.

Hsu et al, "The Use of Antiavidin Antibody and Avidin-Biotin-Peroxidase Complex in Immunoperoxidase Techniques", American Journal of Clinical Pathology, 75(6) (1981), pp. 816–821, Chemical Abstract 95:128730s.

Green, "Bifunctional Reagents and the Quanternary Structure of Protein", Biochemical Journal 104(3), (1967), p. 64.

Vector Laboratories, "Lectins and Biotin-Avidin System", Vector Labs Inc., 1429 Rollins Road, Burlingame, CA 94010.

*Primary Examiner*—Charles F. Warren
*Assistant Examiner*—J. E. Tarcza
*Attorney, Agent, or Firm*—Townsend & Townsend

[57] ABSTRACT

An enhanced labelling complex for localizing markers on a prepared tissue section is disclosed. The complex includes both avidin components and biotinylated macromolecular components at a ratio preselected to provide a complex which is sufficiently large to include a large number of labels, and sufficiently small to penetrate the tissue section. The markers are localized by first introducing a biotinylated link into the tissue section and thereafter exposing the section to the labelling complex.

9 Claims, No Drawings

METHOD AND SUBSTANCE FOR THE ENHANCED LABELLING OF CELLULAR MATERIAL

BACKGROUND OF THE INVENTION

1. Field of the Invention

The present invention relates generally to histology, and, more particularly, it relates to the composition and use of a labelling complex capable of localizing cellular material present in tissue sections at very low concentrations.

2. Description of the Prior Art

The high binding affinity of biotin for avidin is the basis for a number of bioassays currently in use. It is known, for example, to incubate a biotinylated reagent with a prepared tissue section so that the reagent binds specifically to particular markers present in the tissue sample. By then exposing the tissue section to a labelling compound conjugated to avidin, for example, avidin conjugated to an enzyme or fluorescein, the markers are labelled and can be visualized by conventional methods.

A more sensitive method for localizing (or staining) antigens and other markers is that described in a brochure entitled "Lectins and Biotin/Avidin System" distributed by Vector Laboratories, Inc., of Burlingame, Calif. In that method, a primary antibody is "raised against" the antigen or other marker of interest. The primary antibody (e.g., rabbit IgG against human tumor antigen) is exposed to the prepared tissue specimens and will bind to the tumor antigen wherever present. The tissue sample is next exposed to a biotinylated secondary antibody (e.g., goat IgG raised against rabbit IgG) which results in the binding of two secondary antibodies to each primary antibody. Before addition, each secondary antibody derivatized with a number of biotin molecules which are available for binding with avidin. Thus, using these intermediate antibodies and a labelled avidin molecule and by exposing these reagents in sequence to the tissue sample, a label may be attached to the desired antigen site on the cell. Moreover, this method achieves an amplification in that a number of labelling molecules may be attached to each receptor site on the tissue sample. In this way, low concentrations of antigen may be visually detected.

It is further disclosed in the Vector brochure that rather than using an avidin conjugated label, the biotinylated secondary antibody may be exposed to unconjugated avidin. By then exposing the sample sequentially to a biotinylated label, additional avidin, and more biotinylated label, it is disclosed that an even greater amplification can be achieved. In practice, however, the use of a labelled avidin and the serial addition of avidin and biotinylated label, prove approximately equally sensitive, that is, they can detect equal threshold concentrations of marker sites on the tissue sample.

An alternate immunological staining technique in wide use which does not employ avidin-biotin is the peroxidase-antiperoxidase (PAP) technique. The tissue sample to be examined is first incubated with a primary reagent specific to the markers of interest. Thereafter, the sample is incubated with a secondary antibody raised against the primary reagent. The secondary antibody is present in excess so that the two binding sites of the secondary antibody are not exhausted by attachment to the immobilized primary. Antibody raised against peroxidase is obtained in the conventional manner and is incubated with peroxidase to form a peroxidase-antiperoxidase (PAP) complex. The PAP complex is then incubated with the tissue sample where it binds to the remaining sites on the secondary antibody. The sample is then treated with a reagent to cause a staining reaction with the peroxidase compound.

While the above-described staining techniques have proven successful in many applications, their sensitivity remains somewhat limited. If the method employing biotinylated primary reagent is considered to have an amplification of 1, the PAP technique and the methods employing biotinylated secondary antibodies have been found to have amplifications of approximately 3 and 5–8, respectively. It is desirable to provide a staining technique capable of an even greater amplification and of detecting antigens or other markers in tissue samples at even lower concentrations.

SUMMARY OF THE INVENTION

The present invention is a labelling complex and a method for using that labelling complex for localizing antigens and other markers found in prepared tissue sections. The labelling complex is a lattice-like structure formed from avidin and biotinylated macromolecule. The macromolecule serves a structural role in forming the complex by providing the necessary "bulk" to combine a large number of avidin and biotin molecules. The biotinylated macromolecule will typically be an enzyme, carbohydrate, protein or the like. The macromolecule will typically have a molecular weight in the range from 10,000 to $2 \times 10^6$ daltons, more typically from 25,000 to $6 \times 10^5$ daltons. A labelling molecule, such as a radioactive iodide or fluorescein, may be conjugated to either the macromolecule, the avidin, or both. Alternatively, the macromolecule itself may act as the label, such as when biotinylated enzyme is employed, as in the exemplary embodiment By mixing the aforesaid ingredients in aqueous solution at the proper concentration ratios, a relatively large and stable complex including a relatively large number of the labels will be formed. Some of the complexes formed, however, are sufficiently small so that they are able to penetrate the tissue section to effectively bind with a biotinylated link to the marker. The following concentration ratios are effective in forming the labelling complex of the present invention.

|  | Concentration Ratio[1] |
| --- | --- |
| Effective Range | 1:16 to 1:1 |
| Preferred Range | 1:8 to 1:2 |
| Most Preferred Range | 1:4 to 1:2 |

[1]Ratio of biotinylated macromolecule:avidin in solution based on weight.

The labelling complex of present invention is broadly applicable to the localization of a wide variety of markers, such as antigens, carbohydrates, hormone receptors, toxin receptors and the like, which may be present in a tissue section. The markers are initially bound by a primary reagent specific to the marker under investigation. While the primary reagent may be biotinylated and bind directly to the labelling complex of the present invention, it will often be desirable to utilize a biotinylated secondary antibody to serve as a link between the (unconjugated) primary reagent and the labelling complex. By serially incubating the primary reagent, the secondary antibody and the labelling complex with the tissue section, a large number of the labelling molecules can be bound to each marker site. It has been found that the use of such a complex greatly enhances the ability to localize markers at very low concentrations. If the amplification achieved with the prior art methods lies in the range from 1 to 8, as discussed hereinabove, then the amplification achieved using the method of the present invention is in the range from approximately 40 to 80. The use of a secondary antibody as a "link" also limits interaction between the labelling complex and the tissue which may, in some cases, interfere with the ability of the complex to act as a label. The primary reagent may be an antibody, hormone, toxin, lectin and the like may also act as intermediates for the detection of their respective receptors on the tissue section.

DESCRIPTION OF THE SPECIFIC EMBODIMENT

The detailed explanation of the method of the present invention and the examples pertaining thereto will be made primarily in reference to an avidin:biotinylated enzyme complex formed at the particular ratios which have been found to be effective. The invention, however, is not limited to complexes where an enzyme is the labelling molecule or where an enzyme forms part of the structure of the complex. Instead, the invention includes all such biotin:avidin complexes which include a large number of labelling molecules, yet remain small enough in size to effectively bind to the biotinylated intermediate that has been introduced to the tissue section.

1. Preparation of the Labelling Complex

The labelling complex is prepared by incubating aqueous solutions of avidin and a biotinylated macromolecule (having multiple biotin sites) at the concentration ratios shown hereinabove. The macromolecule, avidin, or both are conjugated to one or more labelling ligands. Alternatively, and as is presently preferred, the macromolecule is an enzyme which itself acts as the label. The complex is formed after incubating the solutions at room temperature for a short period of time, typically 5 to 30 minutes. The complex so formed will remain stable for a period of several days, at least.

The availability of free biotin-binding sites (necessary to bind to the biotinylated receptor) on the complex is brought about by incubating a relative excess of avidin with the biotinylated macromolecule, e.g. enzyme. Such as excess of free avidin molecules, however, decreases the sensitivity of the complex because of the competition between the free avidin molecules in the labelling solution and the labelling complex itself for the biotin moities associated with the biotinylated receptor. Conversely, an excess of biotinylated macromolecule saturates the biotinbinding sites on the avidin molecules, rendering them unable to bind to the biotinylated receptors as described hereinbelow. The compositional ratios set forth hereinabove appear to provide the optimum balancing of (1) number of labelling molecules, (2) size of labelling complexes, and (3) availability of biotin-binding sites on the complex.

It has been found that at the biotinylated macromolecule:avidin ratio of from approximately 1:4 to 1:2, the staining intensity reaches a peak even at very low concentrations of the biotinylated receptor. It has also been found that background staining is minimized at the same concentration ratio. Examples illustrating these characteristics are provided hereinafter.

The superior results obtained from the complex may be attributed to the formation of a large complex containing multiple biotinylated macromolecules (e.g., enzymes). During formation of the complex, avidin acts as a bridge between biotinylated macromolecules, while the macromolecules also link the avidin molecules. Thus, a lattice-like complex containing a number of enzyme labelling molecules is formed.

The labelling complex will typically be provided in a kit including aqueous solutions of avidin and of biotinylated macromolecule, e.g. enzyme, carbohydrate, or protein. The solutions will each have preselected concentrations which lead to the proper concentrations ratio upon mixing. For example, the avidin solution might have a concentration of 10 $\mu$g/ml while the biotinylated macromolecule has a concentration of 2.5 $\mu$g/ml, leading to a concentration ratio of 4:1. The avidin and macromolecule solutions will be admixed with a conventional buffer (e.g., 0.05M Tris, pH7.6) at a dilution in the range from approximately 1:50 to 1:250.

2. Localizing Procedure Using the Labelling Complex

After the labelling complex has been prepared in the above-described manner, it is ready to be used to localize the marker of interest. The preferred method of localizing markers at very low concentration involves the serial incubation of the tissue section with a primary reagent (unconjugated), with a biotinylated secondary antibody raised against the primary reagent, and with the labelling complex. The specific procedure used in the following examples is set forth below.

Tissue sections are prepared in a conventional manner for incubation with the primary reagent. Typically, the tissue sections will be deparaffinized and hydrated using xylene and alcohol. After rinsing, the sections are fixed in 0.3% $H_2O_2$ in methanol for thirty minutes.

After washing, the sections are incubated for twenty minutes with 3% normal non-immune serum from the species from which the secondary antibody is obtained.

After such preparation, the tissue sections are incubated for thirty minutes with primary reagent diluted in buffer. In the case of antigenic markers, the primary reagent is antibody raised against the antigen of interest in the conventional manner. Under certain circumstances, e.g., when the concentration of markers is relatively high, it will be desirable to use biotinylated primary reagent and bind the labelling complex thereto. To achieve maximum amplification and sensitivity, however, it is necessary to carry out the remaining steps as set forth below.

After washing, the sections are incubated for thirty minutes with a biotinylated secondary antibody a pair of which bind to each primary reagent. Such biotinylated secondary antibodies are typically commercially available "broad spectrum reagents" that will bind generally to any antibody raised in a particular animal.

After washing, the tissue sections are next incubated from 10 to 60 minutes with the labelling complex formed in the manner described hereinabove.

In the case of an enzyme labelling compound, such as horseradish peroxidase, the sections are then stained, typically with 0.01% hydrogen peroxide and 0.05% diamino benzidine tetrahydrachloride in 0.05M Tris buffer, pH 7.2. Other labelling compounds are prepared as required by methods that are well known in the art. The slides are then prepared for viewing.

3. Comparison of the Labelling Complex of the Present Invention with those of the Prior Art Referring to Table 1, a comparison of the staining intensity acheived with the prior art methods and the method of the present invention is presented. Tissue sections having known and similar concentrations of antigentic marker thereon are prepared in the manner described hereinabove. A series of the slides are then exposed to primary antibody at varying dilution, from 1:400 to 1:12800. Slides at each concentration are then stained using the PAP technique, the technique generally described in the aforementioned Vector Laboratories brochure and the technique of the present invention as set forth above. The intensity of staining was graded on a semi-quantitative scale of 0 (none) to +++ (intense). As can be observed, the PAP technique yielded intense staining only at the highest concentration of primary antibody and yielded no staining at all at a concentration ratio of 1:3200. Similar results were obtained for the Vector technique. Conversely, the labelling complex of the present invention provided intense staining at 1:1600 and provided observable staining at as low a concentration as 1:6400.

TABLE 1

| METHOD | Dilution of Primary Antibody[1](1:X) | | | | | |
|---|---|---|---|---|---|---|
|  | 400 | 800 | 1600 | 3200 | 6400 | 12800 |
| PAP[2] | +++ | ++ | +-± | 0 | 0 | 0 |
| Vector[3,4] | +++/++ | ++/+ | +-± | 0 | 0 | 0 |
| Label-ling[3,5] | +++ | +++ | +++-++ | ++ | + | 0 |

[1]Rabbit antihuman IgG.
[2]The PAP method was carried out as suggested by DeLellis, et al., "Immunoperoxidase Techniques in Diagnostic Pathology", Am.J.Clin.Pathol. 71:483(1979). The secondary antibody was swine antirabbit IgG (1:50). The PAP complex was at 1:100 dilution.
[3]The secondary antibody was biotinylated swine antirabbit IgG (1:200)
[4]Label introduced to secondary antibody by serial addition of avidin (5 μg/ml) and biotinylated peroxidase 5 μg/ml).
[5]Labelling complex formed by mixing avidin D (10 μg/ml) and biotinylated horseradish peroxidase (2.5 μg/ml) (both available from Vector Laboratories, Burlingame, California).

4. Effect of Varying the Biotinylated Enzyme: Avidin Concentration Ratio

Referring now to Table 2, the effect of varying the concentration ratio of avidin:biotinylated enzyme in forming the labelling complex is illustrated. In all cases, rabbit antihuman IgG was the primary antibody (1:800) and biotinylated swine antirabbit IgG (1:200) was the secondary antibody. The intensity of staining was graded on a semi-quantitative scale, 0 (none) to +++ (infense). Observable staining occurs with an avidin:biotinylated peroxidase ratio as high as 16:1 and as low as 1:1. Maximum intensity staining occurs generally with a ratio in the range from 2:1 to 4:1. However, high absolute concentrations of avidin and biotinylated peroxidase appear to lead to background staining.

TABLE 2

|  |  | Concentrations[1] of Avidin (μg/ml) | | | | |
|---|---|---|---|---|---|---|
|  |  | 40 | 20 | 10 | 5 | 2.5 |
| Concentrations[1] (μg/ml) of biotinylated-peroxidase | 1.25 | 0 | 0 | ++ | ++ | + |
|  | 2.5 | +(2) | ++ | +++ | + | + |
|  | 5 | ++(2) | +++ | +++ | + | 0 |
|  | 10 | +++(2) | ++ | + | 0 | 0 |
|  | 20 | +++(2) | + | 0 | 0 | 0 |

[1]20 μl of both avidin solution and biotinylated-peroxidase solution were admixed with 10 ml of buffer.
[2]Background staining is present.

Although the best mode contemplated for carrying out the present invention has been herein shown and described, it will be appreciated that variations and modifications may be made without departing from what is regarded to be the subject matter of the present invention.

What is claimed is:

1. A method for localizing markers on a prepared tissue section, said method comprising:
   exposing the tissue section to a primary reagent capable of specifically binding to the marker;
   exposing the tissue section to biotinylated antibody raised against the primary reagent;
   exposing the tissue section to a preformed labelling complex formed by reacting avidin and a biotinylated macromolecules, wherein at least some of said biotinylated macromolecules are detectable enzymes and said avidin and said biotinylated macromolecules are present at a weight ratio in the range from 1:1 to 16:1; and
   localizing the marker by reacting the detectable enzyme with substrate and observing the reaction.

2. A method for localizing markers on a prepared tissue section, said method comprising:
   introducing a biotinylated reagent into the tissue section, said reagent capable of binding to the tissue section substantially at the marker site;
   exposing the tissue section to the labelling complex comprised of avidin which has been reacted with a preselected amount of a biotinylated enzyme, wherein the weight ratio of avidin to the biotinylated enzyme, reacted was in the range from 1:1 to 16:1, respectively; and
   detecting the enzyme by reaction with substrate.

3. A labelling complex for binding to a biotinylated receptor introduced onto a biological specimen, said complex comprising avidin which has been reacted with a preselected amount of a biotinylated enzyme, wherein the weight ratio of avidin to the biotinylated enzyme reacted was in the range from a 1:6 to 16:1, respectively.

4. A labelling complex as in claim 3, wherein the avidin:biotinylated detectable enzyme is in the range from 2:1 to 4:1.

5. A labelling complex as in claim 3, wherein the biotinylated enzyme has a molecular weight in the range from 10,000 to $2 \times 10^6$ daltons.

6. A labelling complex as in claim 3, wherein the biotinylated enzyme has a molecular weight in the range from 25,000 to $6 \times 10^5$ daltons.

7. A labelling complex as in claim 3, wherein the biotinylated enzyme is biotinylated horseradish peroxidase.

8. A kit for preparing a labelling complex for binding to a biotinylated receptor, the kit comprising,
   a preselected quantity of avidin having a predetermined concentration;
   a preselected quantity of biotinylated detectable enzyme having a predetermined concentration; and
   instructions to admix the avidin and the biotinylated enzyme in a buffer solution in amounts so that the resulting weight ratio of avidin:biotinylated enzyme in the buffer prior to reaction is in the range from 1:1 to 16:1.

9. A kit as in claim 8, wherein the instructions specify that the weight ratio of avidin:biotinylated enzyme to be admixed is in the range from 2:1 to 4:1.

* * * * *

UNITED STATES PATENT AND TRADEMARK OFFICE
CERTIFICATE OF CORRECTION

PATENT NO. : 4,684,609
DATED : August 4, 1987
INVENTOR(S) : Su-Ming Hsu and Laurence Raine It is certified that error appears in the above—identified patent and that said Letters Patent is hereby corrected as shown below:

On the title page, left-hand column, at about line 6 and 7, after "[75] Inventor: Su-Ming Hsu, Seekonk, Mass." insert --, and Laurence Raine, Little Compton, Rhode Island--

Signed and Sealed this

Twelfth Day of January, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO.  : 4,684,609

DATED       : August 4, 1987

INVENTOR(S) : SU-MING HSU

Page 1 of 2

It is certified that error appears in the above-identified patent and that said Letters Patent is hereby corrected as shown below:

On the title page, left hand column, at about lines 17-18, before "OTHER PUBLICATIONS" insert the following:

--4,134,792    Bcguslaski et al.    195/99
  4,282,287    Giese et al.         428/07

FOREIGN PATENT DOCUMENTS

5271        Europe-- and on the right hand column, at about lines 11-12, after "game, CA 94010" insert the following:

--Costello et al., "Enhancement of Immune Cellular Agglutination...", Clin. Chem. 25 (1979), p. 1572.

Guesdon et al., "The Use of Avidin-Biotin Interaction in Immunoenzymatic Techniques", J. Histochem. 27 (1979) p. 1131.

UNITED STATES PATENT AND TRADEMARK OFFICE
CERTIFICATE OF CORRECTION

PATENT NO. : 4,684,609
DATED : August 4, 1987
INVENTOR(S) : Su-Ming Hsu

It is certified that error appears in the above-identified patent and that said Letters Patent is hereby corrected as shown below:

Bayer et al., "The Avidin-Biotin Complex as a Tool in Molecular Biology", Trends in Biochemical Science, 3 (1979) p. 11. --.

Signed and Sealed this

Eleventh Day of April, 1989

Attest:

DONALD J. QUIGG

*Attesting Officer*

*Commissioner of Patents and Trademarks*